(12) United States Patent
Fisker et al.

(10) Patent No.: US 9,180,624 B2
(45) Date of Patent: Nov. 10, 2015

(54) COMPUTER-IMPLEMENTED METHOD FOR THREE-DIMENSIONAL REPRESENTATION

(75) Inventors: Rune Fisker, Virum (DK); David Fischer, Stenløse (DK)

(73) Assignee: 3SHAPE A/S, Copenhagen K (DK)

( * ) Notice: Subject to any disclaimer, the term of this patent is extended or adjusted under 35 U.S.C. 154(b) by 638 days.

(21) Appl. No.: 13/579,452

(22) PCT Filed: Feb. 18, 2011

(86) PCT No.: PCT/DK2011/050050
§ 371 (c)(1),
(2), (4) Date: Oct. 26, 2012

(87) PCT Pub. No.: WO2011/100978
PCT Pub. Date: Aug. 25, 2011

(65) Prior Publication Data

US 2013/0041629 A1    Feb. 14, 2013

Related U.S. Application Data

(60) Provisional application No. 61/306,176, filed on Feb. 19, 2010.

(30) Foreign Application Priority Data

Feb. 19, 2010  (DK) .................... 2010 00143

(51) Int. Cl.
G06F 17/50 (2006.01)
B29C 67/00 (2006.01)
A61C 13/00 (2006.01)

(52) U.S. Cl.
CPC ......... B29C 67/0088 (2013.01); *A61C 13/0004* (2013.01)

(58) Field of Classification Search
CPC .................. A61C 13/0004; B29C 67/0088
USPC .......................................................... 703/1
See application file for complete search history.

(56) References Cited

U.S. PATENT DOCUMENTS

| 4,554,635 A | * | 11/1985 | Levine ........................ 700/183 |
| 5,662,566 A | * | 9/1997 | Marxrieser et al. ............ 483/1 |

(Continued)

FOREIGN PATENT DOCUMENTS

| EP | 1 878 404 A1 | 1/2008 |
| KR | 2010 0059325 A | 6/2010 |
| WO | WO 2008008647 A1 * | 1/2008 |

OTHER PUBLICATIONS

International Search Report (PCT/ISA/210) issued on May 17, 2011, by the Danish Patent Office as the International Searching Authority for International Application No. PCT/DK2011/050050.

(Continued)

*Primary Examiner* — Mohammad Ali
*Assistant Examiner* — Yuhui R Pan
(74) *Attorney, Agent, or Firm* — Buchanan Ingersoll & Rooney PC

(57) ABSTRACT

Disclosed is a computer-implemented method of arranging three-dimensional virtual designs configured to be manufactured as physical designs on a production batch, the method including: providing the virtual designs, where each virtual design is based on a three-dimensional representation of an object, and where at least a number of the virtual designs belongs to a group, where the virtual designs in a respective group satisfy at least one common criterion; and arranging the virtual designs relative to the production batch.

35 Claims, 14 Drawing Sheets

(56) References Cited

U.S. PATENT DOCUMENTS

| | | |
|---|---|---|
| 6,788,986 B1 * | 9/2004 | Traber et al. ............ 700/98 |
| 2003/0074174 A1 * | 4/2003 | Fu et al. ............ 703/13 |
| 2003/0096214 A1 * | 5/2003 | Luthardt et al. ............ 433/171 |
| 2007/0048689 A1 * | 3/2007 | Holzner et al. ............ 433/229 |
| 2008/0260918 A1 | 10/2008 | Lai et al. |
| 2010/0268373 A1 * | 10/2010 | Tremoureux et al. ............ 700/187 |

OTHER PUBLICATIONS

Danish Search Report issued on Oct. 1, 2010 for Application No. PA 2010 00143.

* cited by examiner

COMPUTER-IMPLEMENTED METHOD FOR THREE-DIMENSIONAL REPRESENTATION

This invention generally relates to a computer-implemented method of arranging virtual designs to be manufactured as physical designs on a production batch. More particularly, the invention relates to that the physical designs are arranged optimally on the production batch with respect to material utilisation and/or in groups of designs that satisfy at least one common criterion.

The traditional methods of arranging designs on a production batch comprises that the designs are arranged by a person. The person thus allocates the different designs to different positions on the production batch and how optimal the placement is, is determined and restricted by the skills of the person allocating the designs.

Thus it remains a problem to provide a more efficient method of arranging designs on a production batch which is not restricted by the skills of the person performing the allocation.

Disclosed is a computer-implemented method of arranging three-dimensional virtual designs configured to be manufactured as physical designs on a production batch, the method comprising:
 providing the virtual designs, where each virtual design is based on a three-dimensional representation of an object, and where at least a number of the virtual designs belongs to a group, where the virtual designs in a respective group satisfy at least one common criterion; and
 arranging said virtual designs relative to the production batch.

The method may comprise automatically allocating each virtual design belonging to a respective group to an area for the respective group on the production batch, where the area adapts to the group The allocation of the designs may be such that each virtual design belonging to a respective group is allocated in a position on the production batch such that the physical design is arranged physically together with its respective group on the production batch.

Disclosed is a computer-implemented method of arranging virtual designs to be manufactured as physical designs on a production batch, where the physical designs are arranged optimally on the production batch with respect to material utilisation, and wherein the method comprises:
 providing the virtual designs, where each design is unique and different from the other designs on the production batch, and where at least a number of the designs belongs to a group, where the designs in a respective group satisfy at least one common criterion; and
 automatically allocating each virtual design belonging to a respective group to an area for the respective group on the production batch, where the area adapts to the group.

Disclosed is a computer-implemented method of arranging three-dimensional virtual designs configured to be manufactured as physical designs on a production batch, the method comprising:
 providing the virtual designs, where at least a majority of said virtual designs are unique and different from other designs on the production batch and each virtual design is based on a three-dimensional representation of an object, and where at least a number of the designs belongs to a group, where the virtual designs in a respective group satisfy at least one common criterion;
 arranging said virtual designs relative to the production batch; and
 automatically allocating each virtual design belonging to a respective group to an area for the respective group on the production batch, where the area adapts to the group.

In the context of the present invention, the phrase "the majority of said virtual designs are unique" may refer to the case where more than about 50% of the virtual designs are unique, such as more than about 60%, such as more than about 70%, such as more than about 80%, such as more than about 90%, such as more than about 95%, such as more than about 98%, such as more than about 99%, such as more than about 99.9%.

In some embodiments, the three-dimensional representation is obtained by scanning the object.

Disclosed is a production batch, said batch comprising two or more physical designs manufactured from virtual designs, wherein said designs are arranged and/or allocated in the production batch using the method according to the present invention.

Disclosed is a production batch, said batch comprising two or more physical designs manufactured from virtual designs, wherein said designs are arranged such that a minimal batch height of the production batch is obtained.

Disclosed is a production batch, said batch comprising two or more physical designs manufactured from virtual designs, wherein said designs are arranged on the production batch according to a rule.

Disclosed is a system for arranging three-dimensional virtual designs, where said designs are configured to be manufactured as physical designs on a production batch, where at least a number of the virtual designs belongs to a group, where the virtual designs in a respective group satisfy at least one common criterion, the system comprising:
 an arranging device capable of arranging said virtual designs relative to the production batch using the method according to the present invention; and
 an allocating device capable of automatically allocating each virtual design belonging to a respective group to an area for the respective group on the production batch, where the area adapts to the group.

The system may be capable of receiving virtual designs from an external device.

The system comprise may comprise a model generating device capable of generating a virtual design from a three-dimensional representation of an object.

In some embodiments, the physical designs are arranged optimally on the production batch with respect to material utilisation.

In some embodiments, each virtual design is unique and different from the other virtual designs manufactured as physical designs on the production batch.

In some embodiments, the three-dimensional representation of an object comprises a point cloud. The point cloud may comprise a set of vertices in a three-dimensional coordinate system.

The three-dimensional representation of an object may comprise a 3D surface. The 3D surface may be formed from a point cloud by surface reconstruction.

Consequently, it is an advantage of one embodiment of the method that the shape, form, nesting and physical extent of the different groups can change adaptively, i.e. each group may adapt continuously and constantly to the number of designs, to the size and to the shape of the individual designs in group and to the shapes and sizes of the other groups. Thus the areas may change in an adaptive manner with respect to the groups.

It may be an advantage that the borders between the groups are not fixed, steady, permanent, rigid or regular, but that they can change adaptively.

It may be an advantage that the group shapes and sizes or nesting constantly and continuously changes during the arrangement in order to adapt the group each time a new design is allocated to the production batch. Thus in one embodiment, each area will change size and shape during the allocation process.

Thus the respective area for each group may not be defined in advance; or the area may be defined in advance, but may then be subject to changes during the allocation process.

The allocation process may be an iterative process, where one design is placed at a time. The number of designs to be manufactured on the specific production batch may be known in advance or may not be known in advance.

Furthermore, it is an advantage that the method provides that a very high level of automation is available, and the method furthermore empowers non-technical operators to run a streamlined production. Optimal placement does not only reduce manpower and skill requirements, but also improves material utilization and increases manufacturing capacity, resulting in cost minimisation.

Furthermore it may be an advantage that when the different designs are arranged in groups on the production batch it is very easy and fast for an operator or user to pass on or transmit the designs to their next process point or destination, because the designs are sorted already in groups.

It is a further advantage that the allocation of the designs to the production batch can be performed very quickly by this method.

Virtual designs may be defined as a design which is made as a computer-aided-design (CAD), and which is viewable on e.g. a computer screen. Physical designs may be defined as the physical, manufactured designs. Designs may in general be defined as virtual designs, physical designs etc.

As a majority of the designs are unique, such as each design is unique and different from the other designs on the production batch, the method differentiates from generic production, where the same design is produced on a production batch.

In some embodiments each virtual design is designed based on a three-dimensional representation of an object, where the three-dimensional representation is obtained by scanning the object.

In some embodiments the method comprises allocating each virtual design belonging to a respective group at a position on the production batch, such that the physical design is arranged physically together with its respective group on the production batch.

In some embodiments the optimal arrangement comprises optimal placement, orientation, and/or support generation.

In some embodiments the designs are three dimensional designs.

In some embodiments the method is suitable for mass customization manufacturing.

In some embodiments the manufacturing process comprises one of the following:
3D printing;
milling;
moulding;
sintering.

In some embodiments the designs are of dental restorations.

In some embodiments the designs are configured to comprise more than one single part.

For a dental restoration this may for example be a bridge consisting of three parts connected to each other.

In some embodiments the designs are of hearing devices for ear canals.

In some embodiments the production batch is a blank for milling.

In some embodiments the production batch is a mould for moulding.

In some embodiments the production batch is a plate for 3D printing.

In some embodiments the allocation of designs on the production batch is based on at least one parameter.

In some embodiments the at least one parameter is:
safety distance to a fixture of the production batch;
minimum distance to a boundary of the production batch;
connection thickness between designs on the production batch;
reserved space thickness on production batch; or
sprue basement.

In some embodiments the at least one criterion comprises that the designs belong to one of the following:
common laboratory;
common clinic;
common employee;
common material;
common height;
common patient;
common manufacturing equipment;
common colour;
common post-processing;
common delivery address;
common dentist;
common shipping date;
common size;
common creation date;
common delivery date;
common importance level;
common type of dental preparation, such as coping, bridge etc.
common receiving date.

An advantage of this embodiment is that the common criterion can be anything, which provides an easy, suitable or fast determination of what should happen to the designs, when they have been manufactured. The criterion can be anything that the dental lab or the dental technician or operator or user of the manufacturing machine wishes to sort the designs after. If the dental lab is a big lab serving a lot of dentists, then the criterion can advantageously be for example the individual dentists or patients at the dentists. If the designs should be post-processed with a coating or colouring etc. then the criterion can advantageously be one of these things. If the manufacturing machine can be adjusted or modified to different parameters, such as height of the production batch, height of the physical design etc., then the criterion can advantageously be related to these parameters for providing an efficient and optimal manufacturing.

In some embodiments, the method comprises arranging the virtual designs in a virtual batch such that their arrangement both relative to each other and relative to the production batch may be configured to be optimized in the virtual batch before being manufactured on the physical production batch.

The virtual batch may extend over a batch plane and have a batch height. The dimensions of the virtual batch may differ from the dimensions of the production batch. For instance, the virtual batch may be larger than the production batch, such that the virtual designs can be moved around freely in the virtual batch to obtain an arrangement, which requires a relatively low material consumption.

The method may comprise taking into consideration the three dimensional shape of the designs in the arrangement of the designs.

In some embodiments, the method comprises arranging a predetermined number of virtual designs in a virtual batch, where the virtual designs are configured to be realized as physical designs on a production batch.

In some embodiments, arranging the designs comprises determining a minimal batch height for a given number of designs.

For some production systems it may be preferred that the height of the production batch is kept at a minimum value. This may sometimes be the case when e.g. milling designs from a blank.

The method may comprise optimizing the arrangement of the virtual designs to obtain the minimal batch height for a given number of designs.

For a production batch, which is substantially planar extending over a batch plane and having a substantially constant batch height across said batch plane, the minimizing of the batch height may be achieved by arranging the designs in the productions batch such that elongated designs are arranged with their longitudinal axis defining a non-zero angle to the normal of the batch plane.

Accordingly, the method may comprise arranging the virtual designs in a virtual batch in such a manner that the longitudinal axis of elongated designs defines non-zero angles to the normal of the batch plane.

In the context of the present invention, the height of a design when arranged in a virtual batch or a production batch may be measured as the size of the design perpendicular to the plane of the production batch, i.e. the height may be a cross sectional dimension of the design along a normal to the batch plane.

The method may comprise determining the minimal height of each virtual design which is to be manufactured on a production batch. The minimal height of the individual designs may be determined using techniques know to the person skilled in the art. When the minimal height of each design is determined, a minimal batch height may be determined as the minimal height of the design, which has the largest minimal height.

In some embodiments, the method comprises arranging the virtual designs in the virtual batch such that each design has its smallest possible height and subsequently rotating at least some of the virtual designs relative to the batch plane such that their projection area in the batch plane is reduced while the height of each virtual design is kept under said minimal batch height.

In the context of the present invention, the phrase "rotating relative to the batch plane" may refer to the situation where a design is rotated such that the angle between an axis of the design and the normal of the batch plane changes.

In the context of the present invention, the phrase "rotating in the batch plane" may refer to the situation where a design is rotated such that its projection into the batch plane rotate around the normal of the batch plane.

In some embodiments, all the virtual designs are initially arranged in the virtual batch such that each design has its smallest possible height. Once the minimal batch height is determined, at least some of the designs having a minimal height below the minimal batch height may be rotated relative to the batch plane such that their projected area in the batch plane is reduced. The rotation may cause the height of the design to increase but this may be acceptable as long as its height is below the minimal batch height. This procedure may allow the production of the designs in a production batch with a minimal height while simultaneously reducing the area of the production batch.

For a design which has a preferred orientation in the production batch, the minimal height of that design may be the height of the design when arranged according to the preferred orientation. This may for instance be the case when a crown is milled from a blank, where it may be preferred that the tooth crown is arranged such that the margin line is directed towards the milling section.

In some embodiments, at least one of the designs is for an abutment which may define an insertion direction along which a crown can be positioned on the abutment and an implant direction along which a screw may arrange the abutment in relation to an implant connected e.g. to the jaw bone of a patient.

The implant direction and the insertion direction may be non-parallel, i.e. have an angle relative to each other. Such a design for an abutment may have a preferred orientation relative to the batch plane. In some embodiments, such a design should preferably be arranged such that the angle between the insertion direction and the batch plane substantially equals the angle between the implant direction and the batch plane. The projections of the insertion direction and the implant direction into the batch plane may coincide or they may be arranged in continuation of each other.

In some embodiments, the minimal height of each design is determined by arranging the virtual designs in the virtual batch and rotating the virtual designs relative to the virtual batch. When the minimal height of each virtual design is determined, the minimal height of all designs is compared and the largest minimal height can be noticed.

In some embodiments, the method comprises rotating at least some of the virtual designs relative to the batch plane. When rotated relative to the batch plane their projection area in the batch plane may be reduced.

The rotation of the virtual designs relative to the virtual batch may follow a predefined rotation scheme.

The arranging of the virtual designs in the virtual batch may be governed by indications relating to a characteristic of each design. A design which prior to the arrangement in the virtual batch has been indicated as a small design may be positioned directly without taking into consideration how the design is arranged in order to have its minimal height.

In some embodiments, arranging the designs comprises rotating the virtual designs having a minimal height below the batch height relative to the batch plane. This rotation may be such that the area of the projection of the virtual design into the batch plane is reduced. The method may comprise rotating a least part of the virtual designs relative to the batch plane until the height of each design reaches the minimal batch height or the maximal height of the design.

This rotation of the designs relative to the batch plane may provide the advantage that the designs may be arranged very closely in the production batch thus providing an optimal utilization of e.g. a blank.

In some embodiments, the method comprises arranging the virtual designs based on their projections into the batch plane.

In some embodiments, arranging the designs comprises an in-plane movement of virtual designs in the virtual batch, such as a rotation in the batch plane around the normal to the batch plane and/or a translation in the plane The rotation of the virtual in the batch pane may follow a predefined rotation scheme. The translation of the virtual designs in the virtual batch may follow a predefined translation scheme.

The in-plane movement and/or the rotation relative to the batch plane may be such that an optimal arrangement of the virtual designs in the virtual batch is obtained.

In some embodiments, arranging the designs comprises an iterative procedure wherein at least said in-plane movement or the rotation of the designs relative to the batch plane is performed at least twice, such as e.g. an iterative process comprising a rotation relative to the batch plane, an in-plane movement of the designs, a further rotation relative to the batch plane and a further in-plane movement.

The arranging of the designs may comprise applying one or more rules to the arrangement of the virtual designs in the batch. A rule may relate to the projection of designs into the batch plane and/or on the full three dimensional surface of the designs.

The arranging using one or more rules may be used for the overall nesting of the all the designs on the batch.

In some embodiments, a sequence of rules is applied in the arrangement of the virtual designs. The sequence of rules may be applied to the designs in one group at a time, to larger ensemble of designs or to all designs of the batch.

The rule may relate to the starting position, i.e. where the first design is arranged in the batch, the shape of the track along which the designs are placed in the virtual and/or physical batch, the sorting of the designs, and the direction of change in each group of designs. The direction of change may e.g. be related to a change in the height of the designs, such as in the case where the highest designs are placed before the lower. The direction may be descending or ascending.

The starting point may be chosen to be at the center, at the edge or at a position between the center and the edge of a production batch.

The shape of the track along which the designs are placed in the batch may comprise a spiral, where each following design may be arranged in a neighbouring position on the spiral relative to the previous design. The shape of the track may in principle comprise any kind of shape, such as a square shaped or a circular shaped pattern.

The sorting of the designs may relate to said at least one criterion, to the production tolerance, or to physical properties of the designs, such as the height, length, mass, mass density or shape of the designs.

In some embodiments, the method comprises applying a rule which sets an upper limit to the maximal length of coherent sections with designs before a section free of designs is introduced to provide stability to the production batch.

In some embodiments, the method comprises applying a rule relating to the orientation of the designs relative to the circumference of the production batch. The rule may provide that a majority of the designs are arranged at a specific angle relative to the circumference, such as the designs having a side which is substantially parallel to circumference, or such as the designs having a side which is substantially perpendicular to circumference.

In some embodiments, the method comprises applying a rule relating to the relative orientation of the designs such as the designs being arranged with similar or alternating orientations relative to their nearest neighbours.

In some embodiments, at least one of the rules is applied at least two times to the virtual designs. The two times may follow each other directly or be separated by the application of one or more other rules. For instance a method may comprise applying a first rule, applying a second rule, and subsequently applying said first rule again.

The manufacture of the physical designs in a production batch may require that the approach line along which the design transferring tool of the production equipment approaches the production batch and the normal of the production batch are arranged at an acute approach angle relative to each other. In such cases, the position where the approach line intersects the top surface of the production batch is displaced in the batch plane relative to the position of the design. In some cases the approach angle for a least some parts of the design is such that a cone-like approach volume may be defined by the full range of approach lines used to manufacture a design. Within this approach volume the design transferring tool, such as the drill of a milling machine, must have unblocked access to the portion of the production batch where the design is formed. In some embodiments, two neighbouring designs are arranged in the batch such that their approach volumes intersect.

In some embodiments, said rule comprises that two neighbouring designs are arranged such that the areas of the approach volumes for the designs at the top surface of the production batch intersects while still having full access to the positions of both designs for the design transferring tool.

In some embodiments, such as when the design is formed using an additive process, such as 3D printing, the designs may be defined in two or more layers in the production batch. For instance, designs according to one criterion may be arranged in the same layer.

In some embodiments the method comprises:
allocating a first virtual design belonging to a first group at a first arbitrary position on the production batch;
allocating a second virtual design belonging to a second group at a second arbitrary position different from the first arbitrary position on the production batch;
allocating a third design belonging to the first group at a third arbitrary position, which is different from the first and the second arbitrary positions on the production batch, and which is in the vicinity of the first arbitrary position;
allocating each successive design belonging to a group at an arbitrary position, which is different from all the previous positions, and which is in the vicinity of its group members on the production batch;
continuously evaluating whether there is more space left on the production batch, and whether there are more designs to be manufactured;
if yes, allocate the designs according to the above step;
if no, stop allocating designs and finalize the arrangement.

An advantage of this embodiment is that the allocation of the designs can be performed very quickly because the positions are arbitrary at first, and later the group members are arranged in the vicinity or neighborhood of the other group members, and the areas of the groups can constantly be adapted to the present group situation and size.

The successive designs may be a four, a fifth, a sixth design etc.

In some embodiments the vicinity is defined as being within a certain distance.

An advantage of this embodiment is that the vicinity or distance can for example be 1 cm, 5 cm, 10 cm etc. depending on the total size of the production batch, depending on the number of different groups, depending on the typical number of designs in a group etc.

The distance between two neighbouring designs may be less than about 10 cm, such as less than about 5 cm, such as less than about 1 cm, such as less than about 0.5 cm, etc. depending on the total size of the production batch, depending on the number of different groups, depending on the typical number of designs in a group etc.

In some embodiments the first allocated design in each group is arranged on the production batch such that there is a suitable area around it for other group members.

In some embodiments the suitable area is determined based on a defined distance between the group members and based on a defined distance to the other groups.

In some embodiments the method comprises that a user can select the defined distances.

An advantage of this embodiment is that the defined distance can take account of the space needed by the specific manufacturing machine for performing the manufacturing, for example some machines may have print heads restricting or providing that the designs are printed in specific rows with a predetermined length and width. Other machines may have specific tools restricting the designs to be manufactured in specific ways and with specific space or distance between designs.

Thus the method may comprise arranging the designs according to one or more parameters of the manufacturing machine In some embodiments the method comprises that a visual border is made between the groups.

An advantage of this embodiment may be that due to the visual border between the groups it is fast and easy for the operator to identify what the further process for a particular group is.

In some embodiments the visual border is a dotted border between the groups. The visual border may comprise a section with no designs, where this region divides different groups. Groups comprising a number of designs may be shaped as rows or clusters.

In some embodiments the method comprises indicating the criterion or an identification of the group at the group.

In some embodiments the method comprises printing the criterion as text or printing an identification of the group within the spatial extent of the group on the blank.

The present invention relates to different aspects including the method described above and in the following, and corresponding methods, devices, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a computer program product comprising program code means for causing a data processing system to perform the method, when said program code means are executed on the data processing system.

Disclosed is also a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

In step 101 the virtual designs to be manufactures as physical designs are provided. At least a number of the designs belong to a group, and the designs in a respective group satisfy at least one common criterion. The virtual designs may be provided as a file from a customer, a partner, a collaborator, from the user's or operator's own design file etc.

In step 102 each virtual design belonging to a respective group is allocated to an area for that respective group on the production batch, and the area is configured to adapt to the group size.

FIG. 2 shows examples of prior art.

Figure 1:
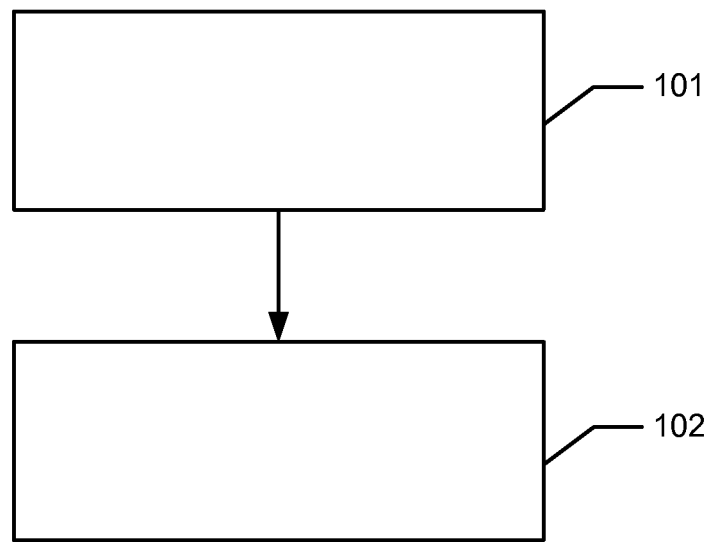
FIG. 1 shows an example of a flowchart of the method.
Figure 2A:
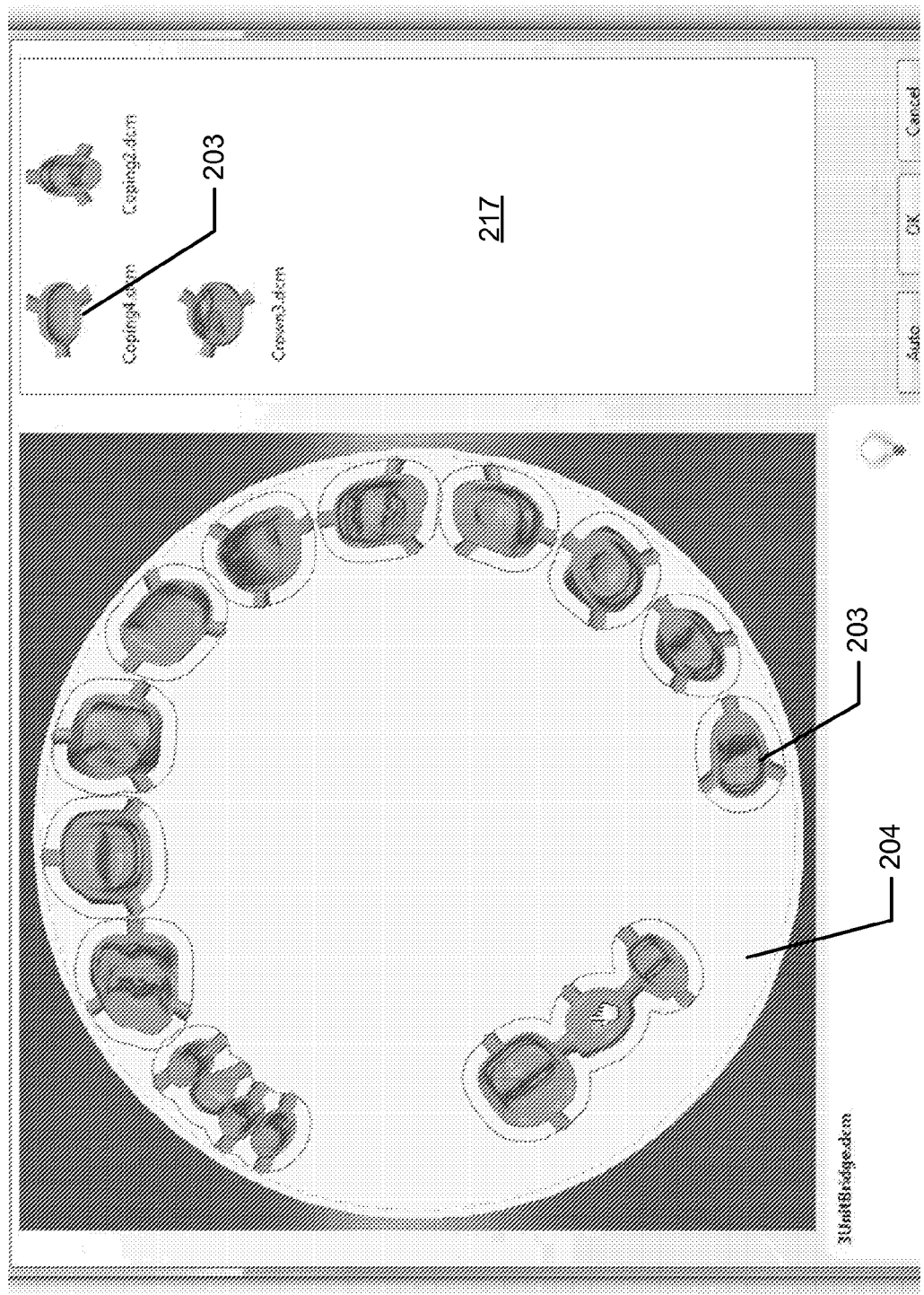
FIG. 2 shows examples of prior art.

In FIG. 2a) it is shown that the designs 203 are allocated to positions on the production batch for manufacturing. The designs 203 which have already been allocated are shown on the production batch 204, and the designs 203 which are waiting to be allocated at the production batch are shown in the region 217 to the right. FIG. 2a) shows a screen-shot from a program in which the designs 203 can be allocated to the production batch.

Figure 2B:
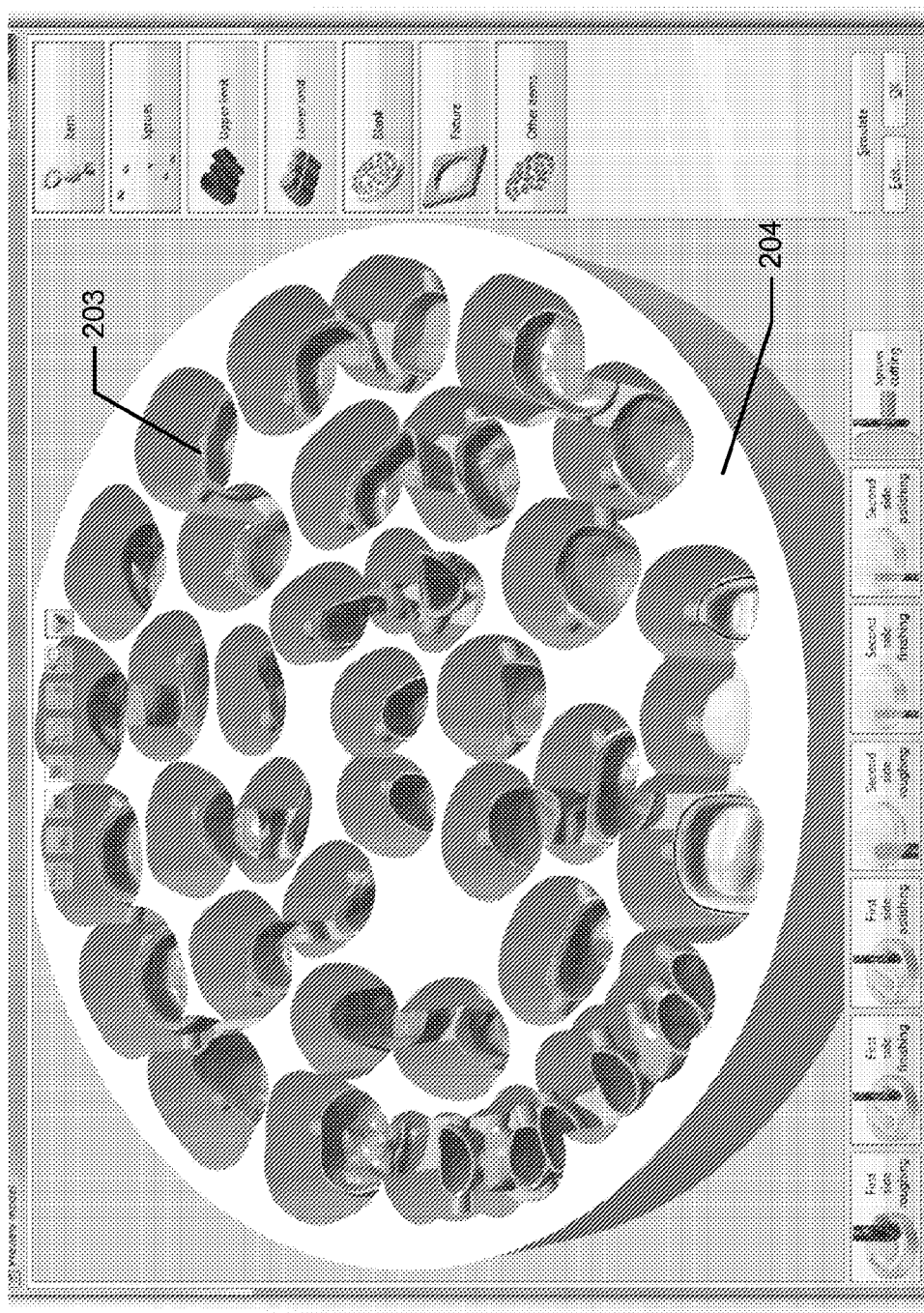

In FIG. 2b) the different designs 203 has been allocated to the production batch 204, and the designs 203 are not arranged together in groups having a common criterion.

In this example the production batch is a blank for milling, and the designs are thus manufactured by milling.

The production batch is shown in a screenshot of a program for controlling a milling machine.

Figure 3:
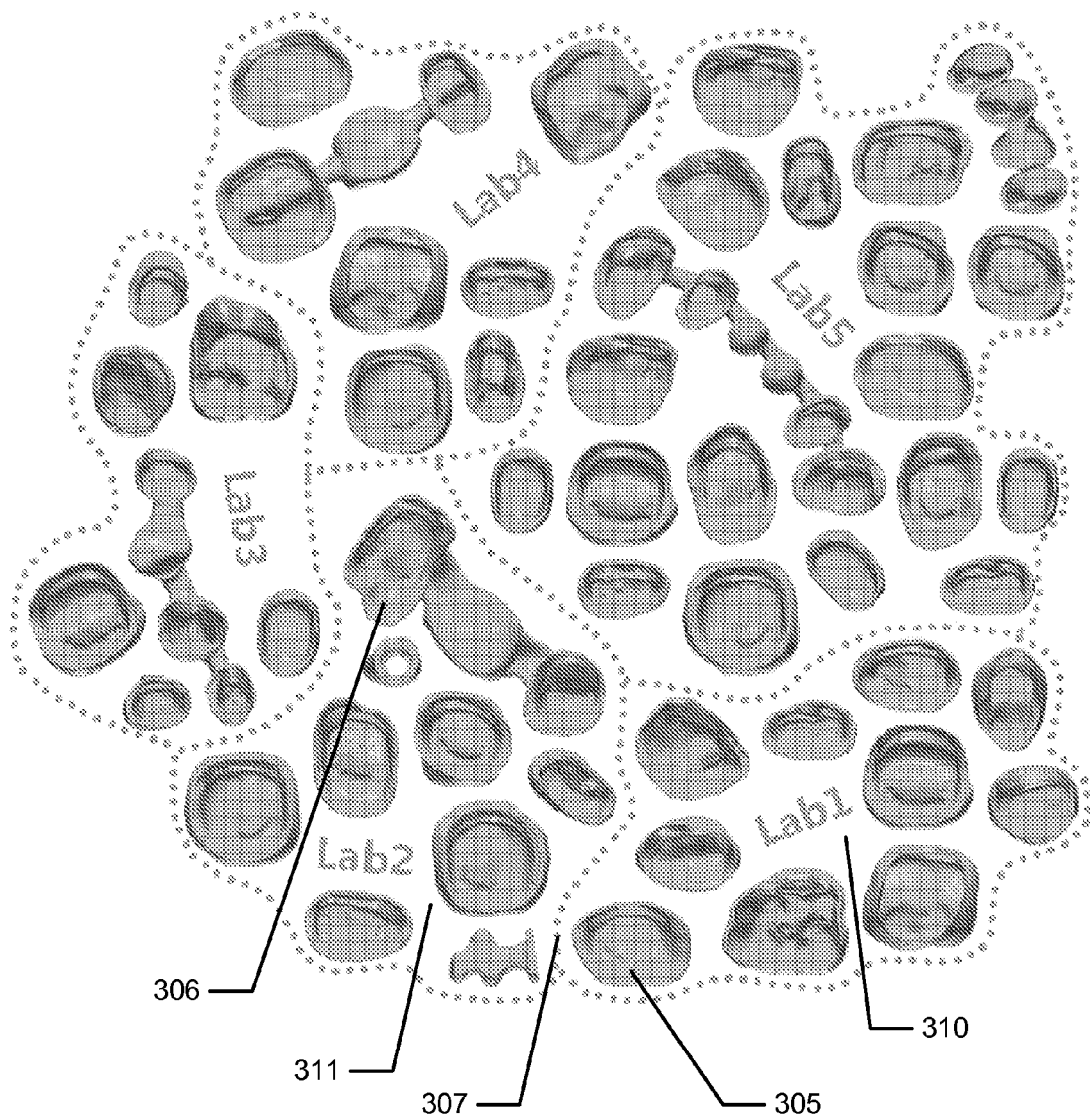
FIG. 3 shows a schematic example of designs arranged in adaptive groups.

FIG. 3 shows a schematic example of designs arranged in adaptive groups.

The designs are dental restorations.

The design 305 belongs to and is arranged in the group 310 called "lab 1" which is denoted in the area or region of the group. Design 306 belongs to and is arranged in the group 311 called "lab 2", which is also denoted in the area or region of the group. Design 305 is an example of a crown, and design 306 is an example of a bridge consisting of three parts. The border 307 between the two groups 310 "lab 1" and 311 "lab 2" is indicated by a dotted line. All designs in this example are arranged in groups and each group name is denoted within the area or region of the group.

The adaptive groups in this example are shaped like clusters or organic forms, they are somewhat round and with soft borders.

Figure 4:
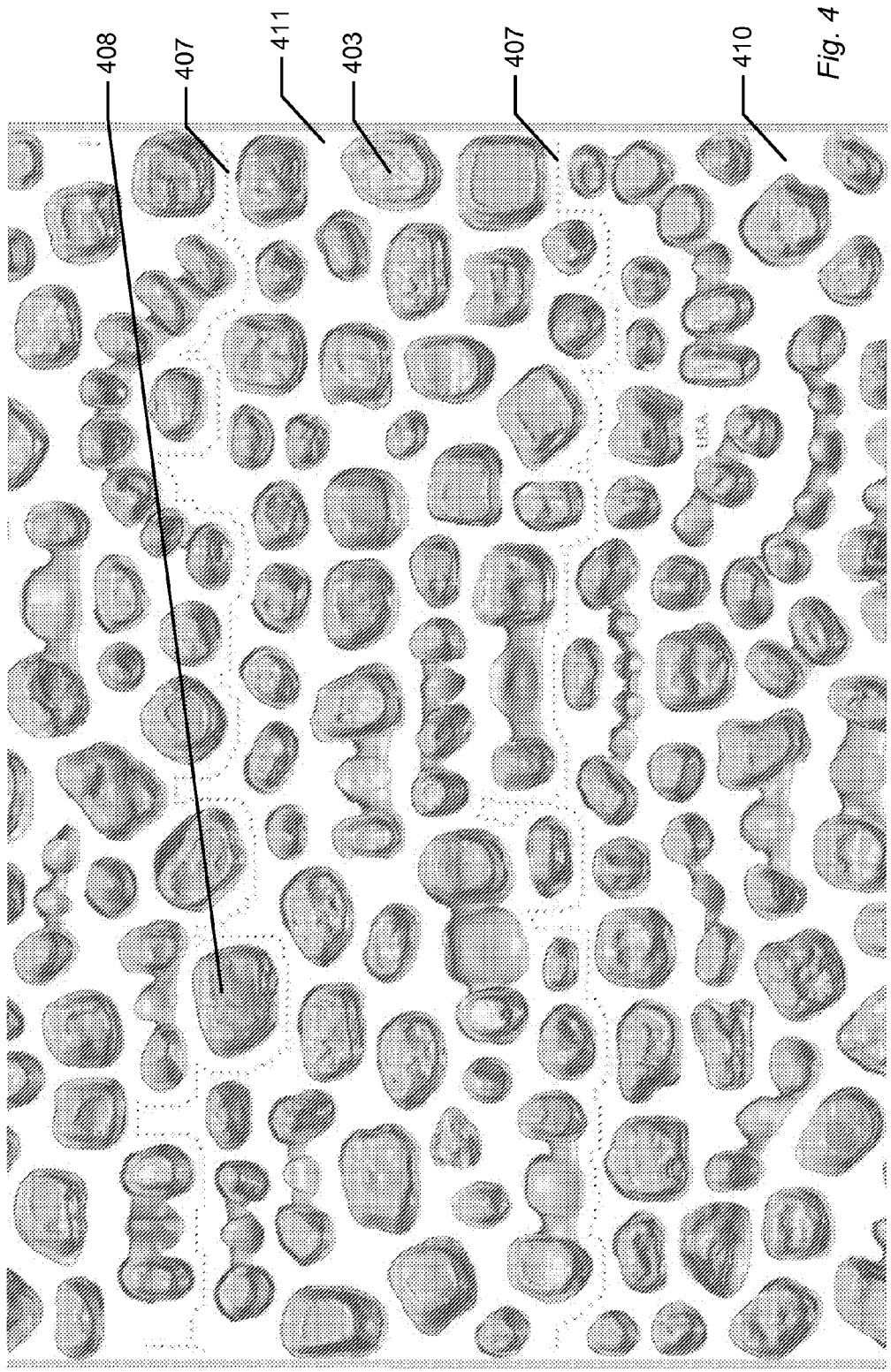
FIG. 4 shows an example of designs arranged in adaptive groups seen from above.

FIG. 4 shows an example of designs arranged in adaptive groups seen from above.

The designs 403 are dental restorations.

The adaptive groups 410, 411 in this example are shaped like wide rows with almost straight lines separating the groups, but also with few designs like 408 which disrupts the straight borders 407.

The figure shows just a section of a production batch.

In the group 410 in the bottom of the batch the text "USA" is denoted on the batch, which can indicate that the designs in this groups should be send to USA after manufacturing.

Figure 5:
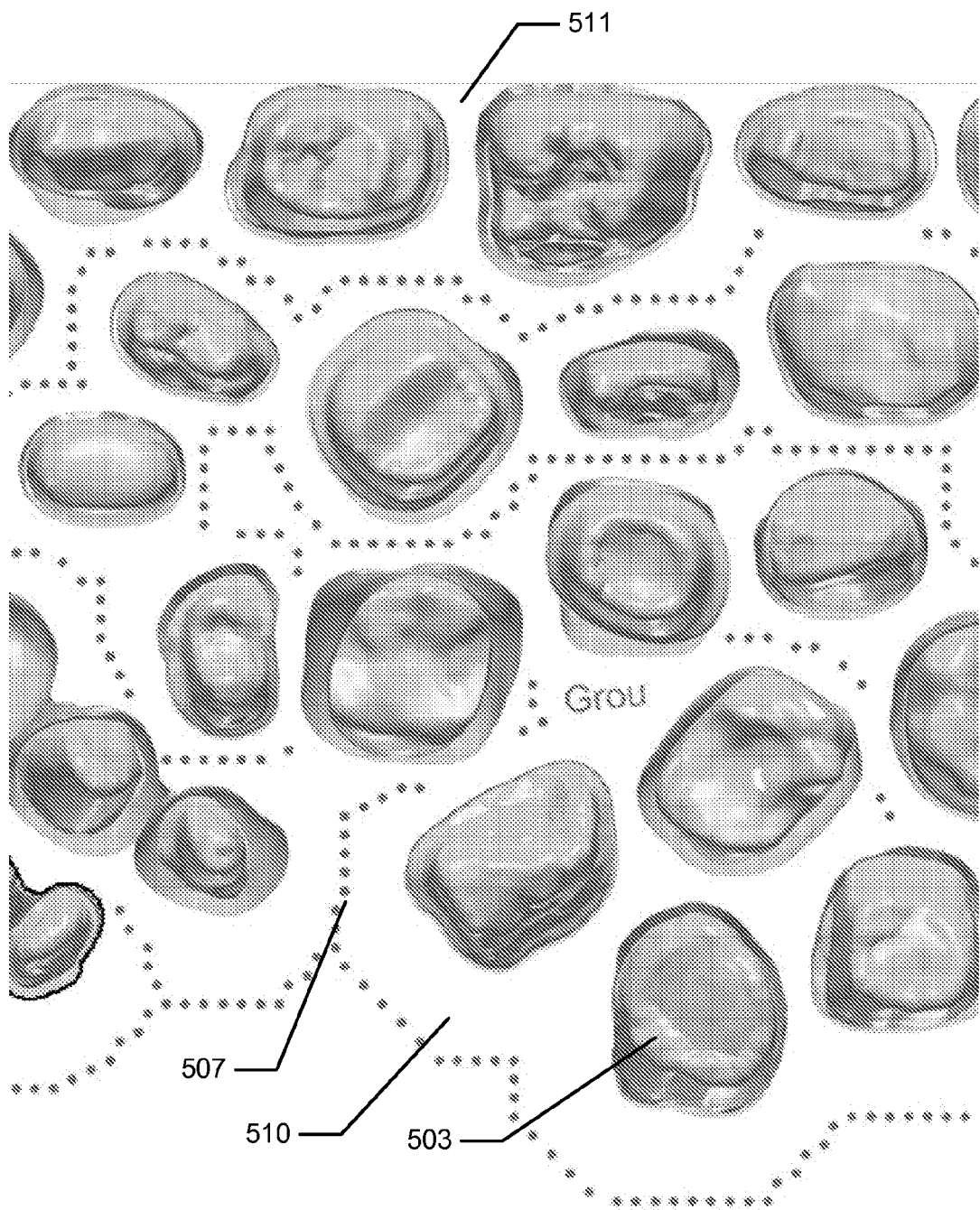
FIG. 5 shows an example of a close-up look of designs arranged in adaptive groups.

FIG. 5 shows an example of a close-up look of designs arranged in adaptive groups.

The designs 503 are dental restorations.

The adaptive groups 510, 511 in this example are a combination of narrow rows with almost straight lines separating the groups, and groups shaped like clusters or organic forms, which are somewhat round but not with soft borders 507.

In this example "Grou" is denoted within group 510 to indicate the common criterion for this group.

Figure 6:
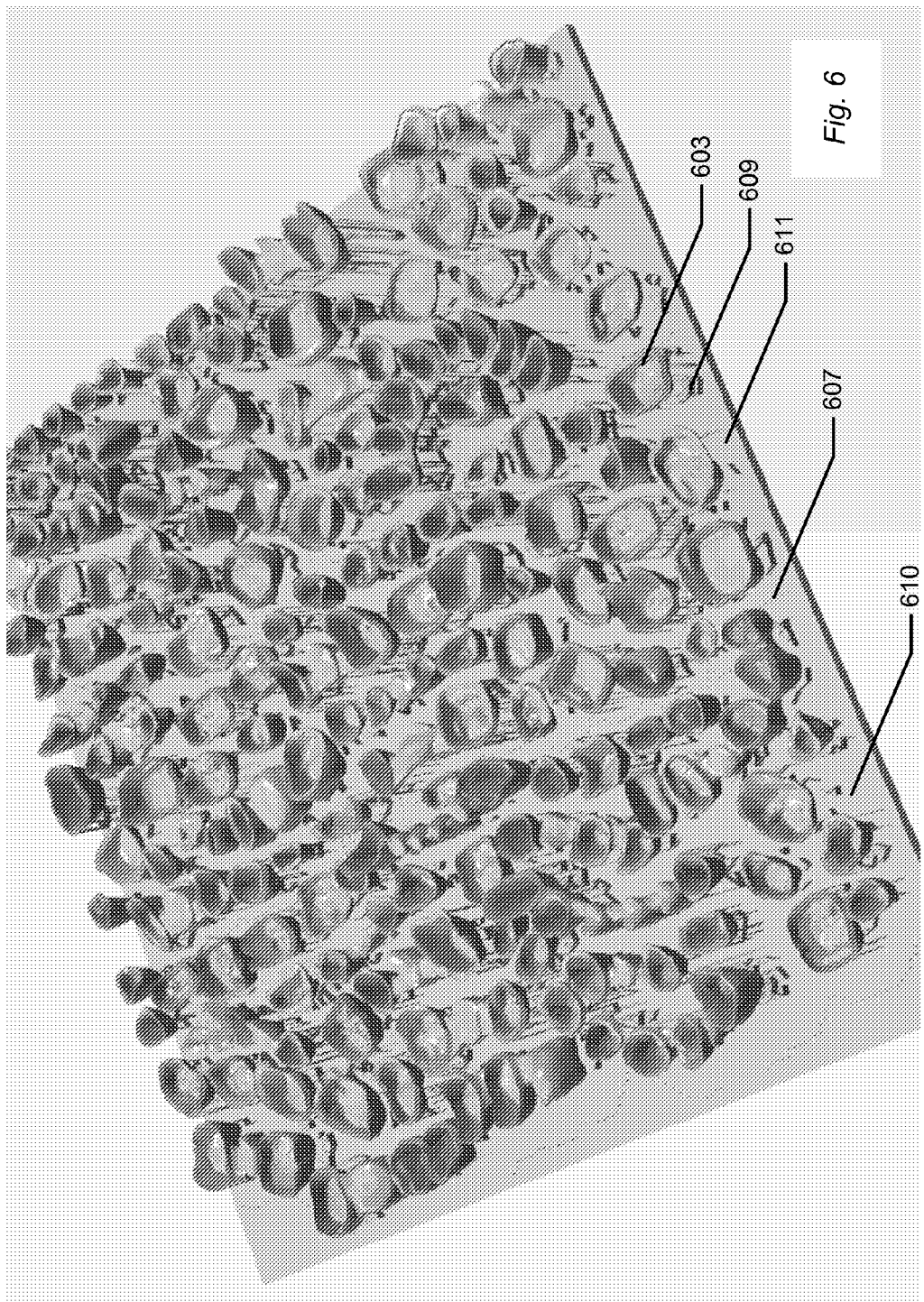
FIG. 6 shows an example of a 3D view of designs arranged in adaptive groups.

FIG. 6 shows an example of a 3D view of designs arranged in adaptive groups.

The designs are dental restorations manufactured by means of 3D printing. When manufacturing designs 603 by 3D printing, the designs 603 may need supports 609 for supporting the designs, which is a result of the manufacturing process.

The borders 607 between the groups 610, 611 are not very clear or distinct in this example, however the groups are generally shaped as wide, substantially straight rows here.

Figure 7:
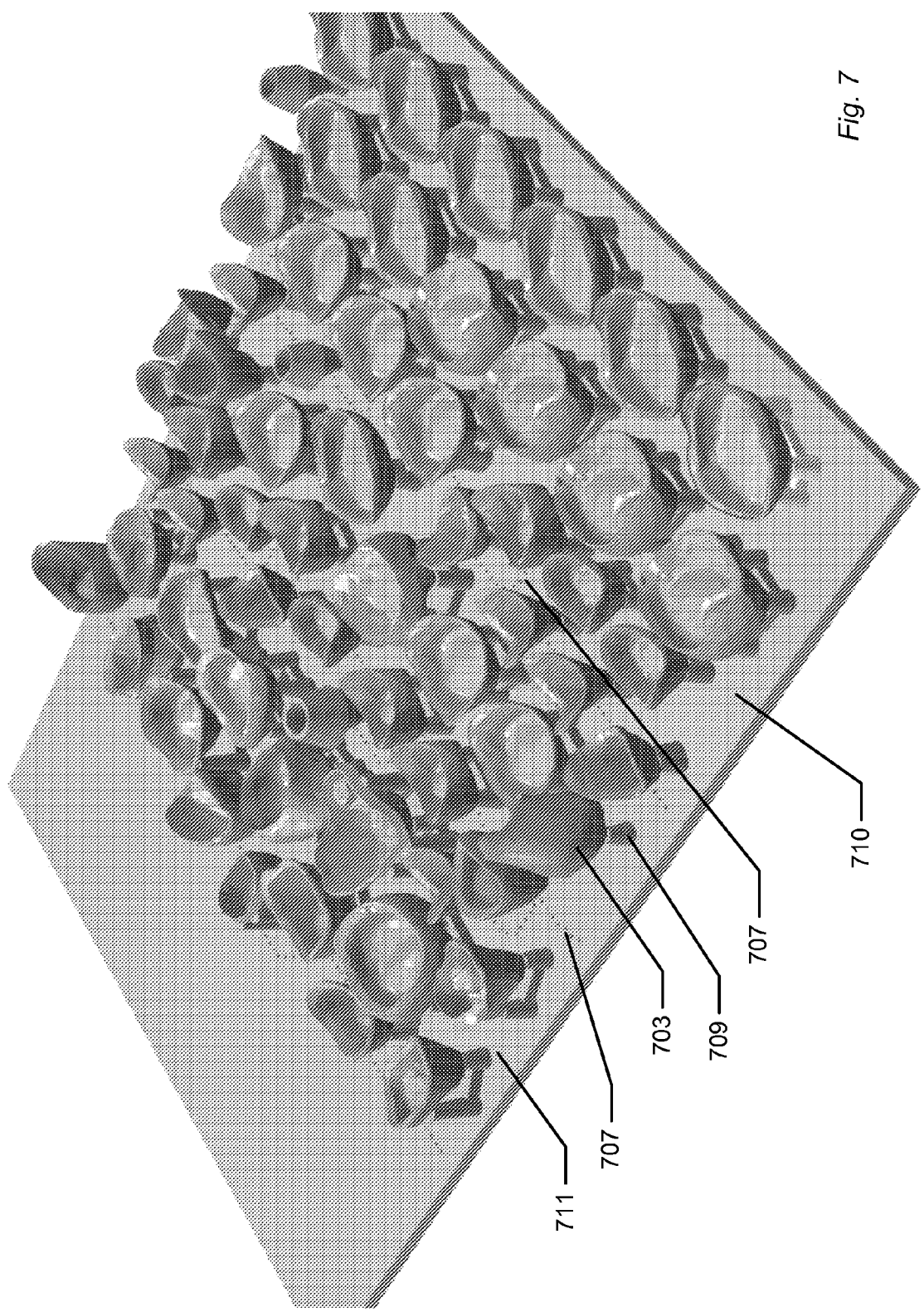
FIG. 7 shows an example of a close-up 3D view of designs arranged in adaptive groups.

FIG. 7 shows an example of a close-up 3D view of designs arranged in adaptive groups.

The designs are dental restorations manufactured by means of 3D printing.

The designs 703 have supports 709 for supporting the designs.

The borders 707 between the groups 710, 711 are in this example generally shaped as wide, substantially straight rows.

Figure 8:
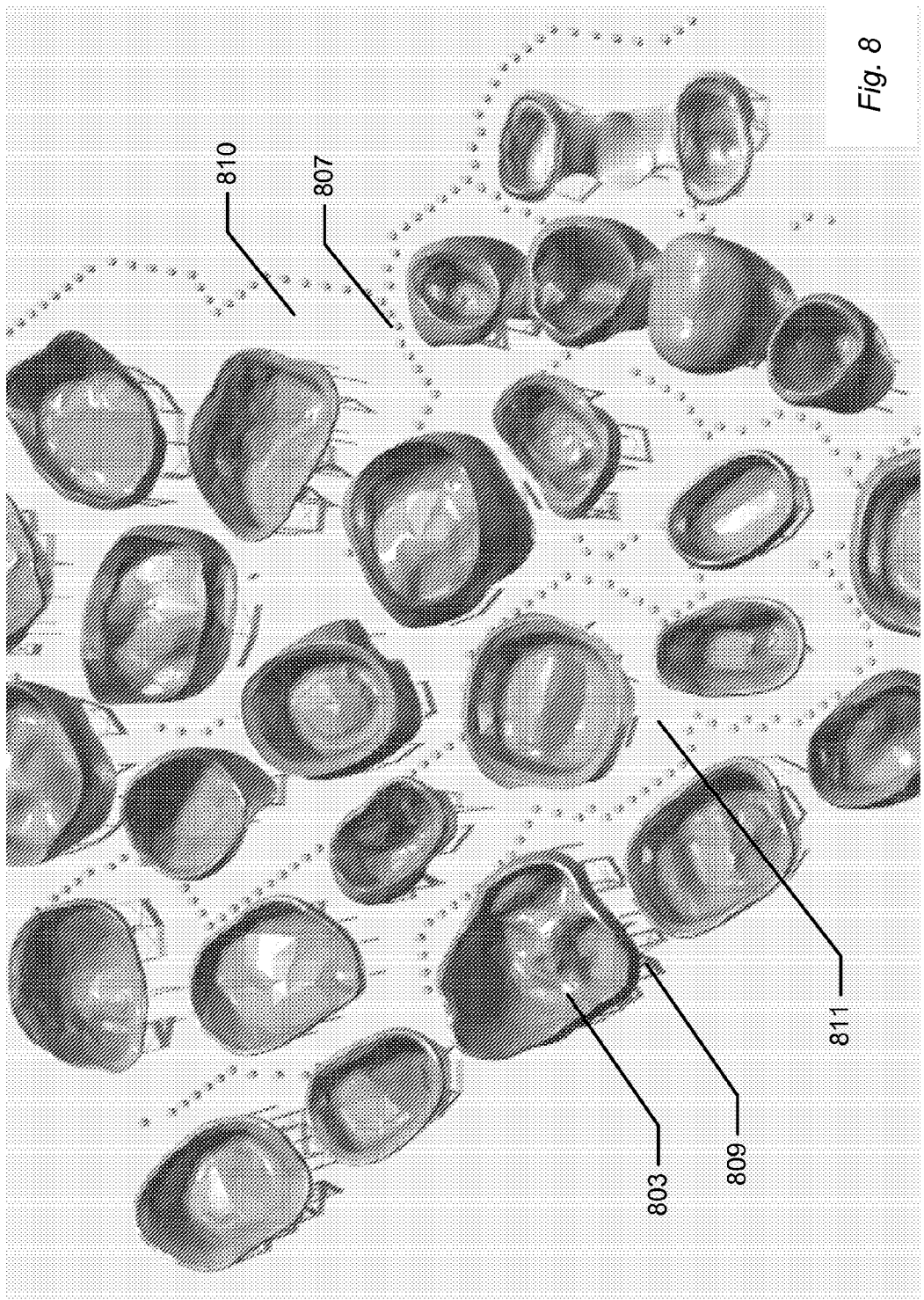
FIG. 8 shows an example of a 3D view of designs arranged in adaptive groups.

FIG. 8 shows an example of a 3D view of designs arranged in adaptive groups.

The designs are dental restorations manufactured by means of 3D printing.

The designs 803 have supports 809 for supporting the designs.

The groups 810, 811 separated by borders 807 are in this example generally shaped as a combination of rows and more cluster-like shapes.

Figure 9:
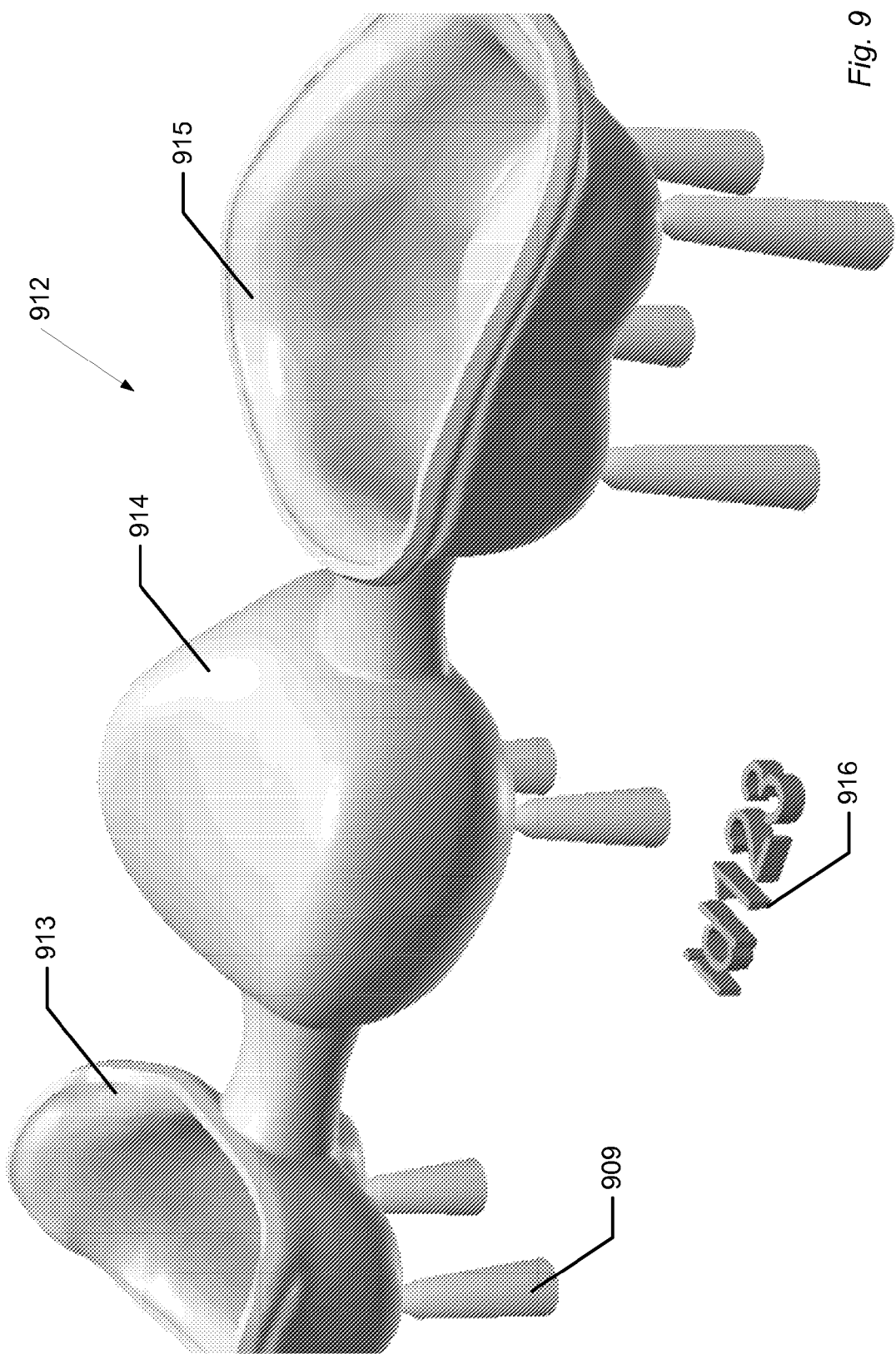
FIG. 9 shows an example of a design of a dental restoration.

FIG. 9 shows an example of a design of a dental restoration.

The dental restoration can be manufactured as a design in an adaptive group. The design is in this example a bridge 912 with three parts 913, 914, 915. The bridge 912 is manufactured by 3D printing, and is supported by support means 909. An identification tag 916 reading "id123" is placed in front of the bridge 912.

Figure 10:
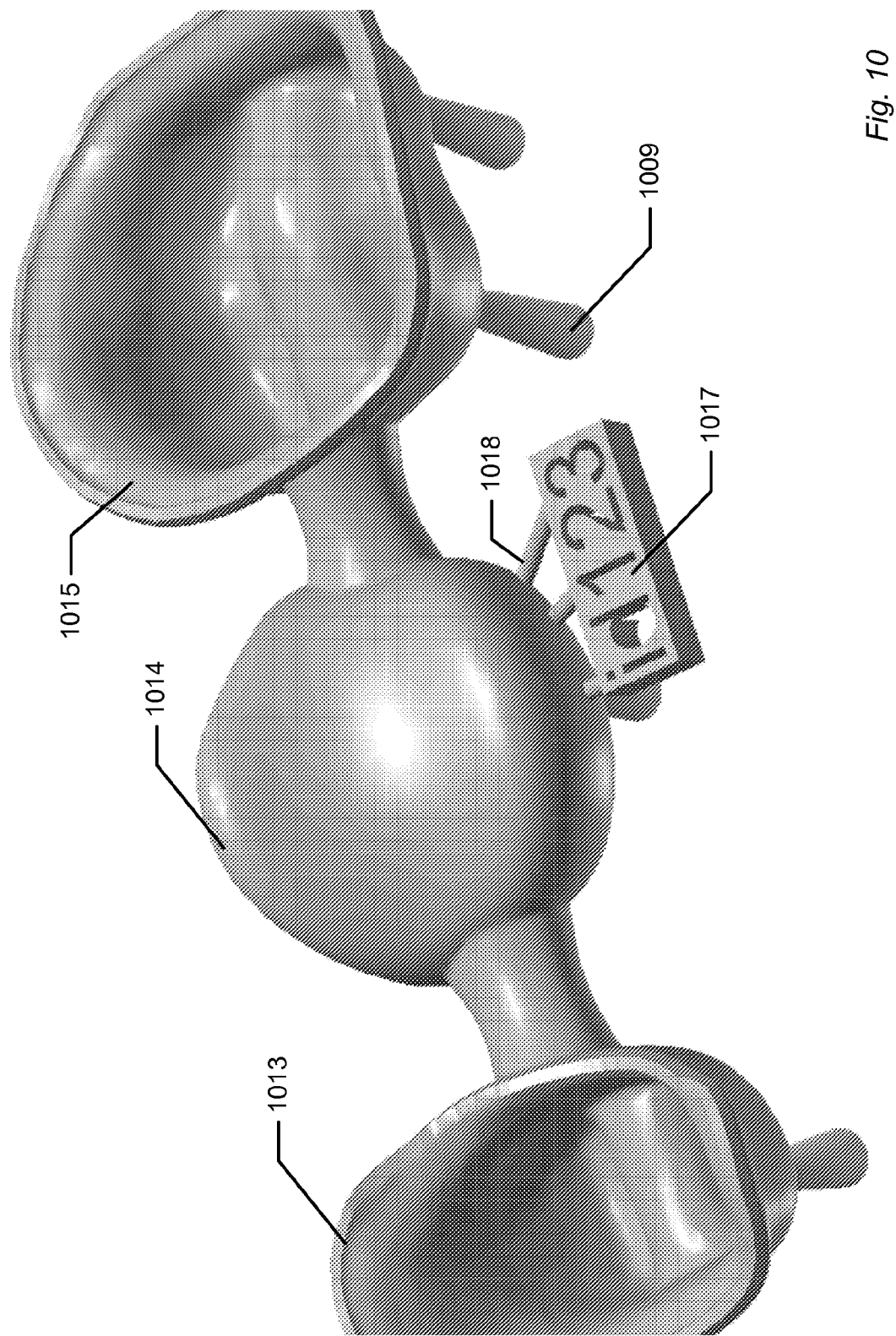
FIG. 10 shows an example of a design of a dental restoration.

FIG. 10 shows an example of a design of a dental restoration.

The dental restoration can be manufactured as a design in an adaptive group. The design is in this example a bridge 1012 with three parts 1013, 1014, 1015. The bridge 1012 is manufactured by 3D printing, and is supported by support means 1009. An identification tag 1017 reading "id123" is placed on part 1014 of the bridge 1012 by means of connectors 1018.

Figure 11:
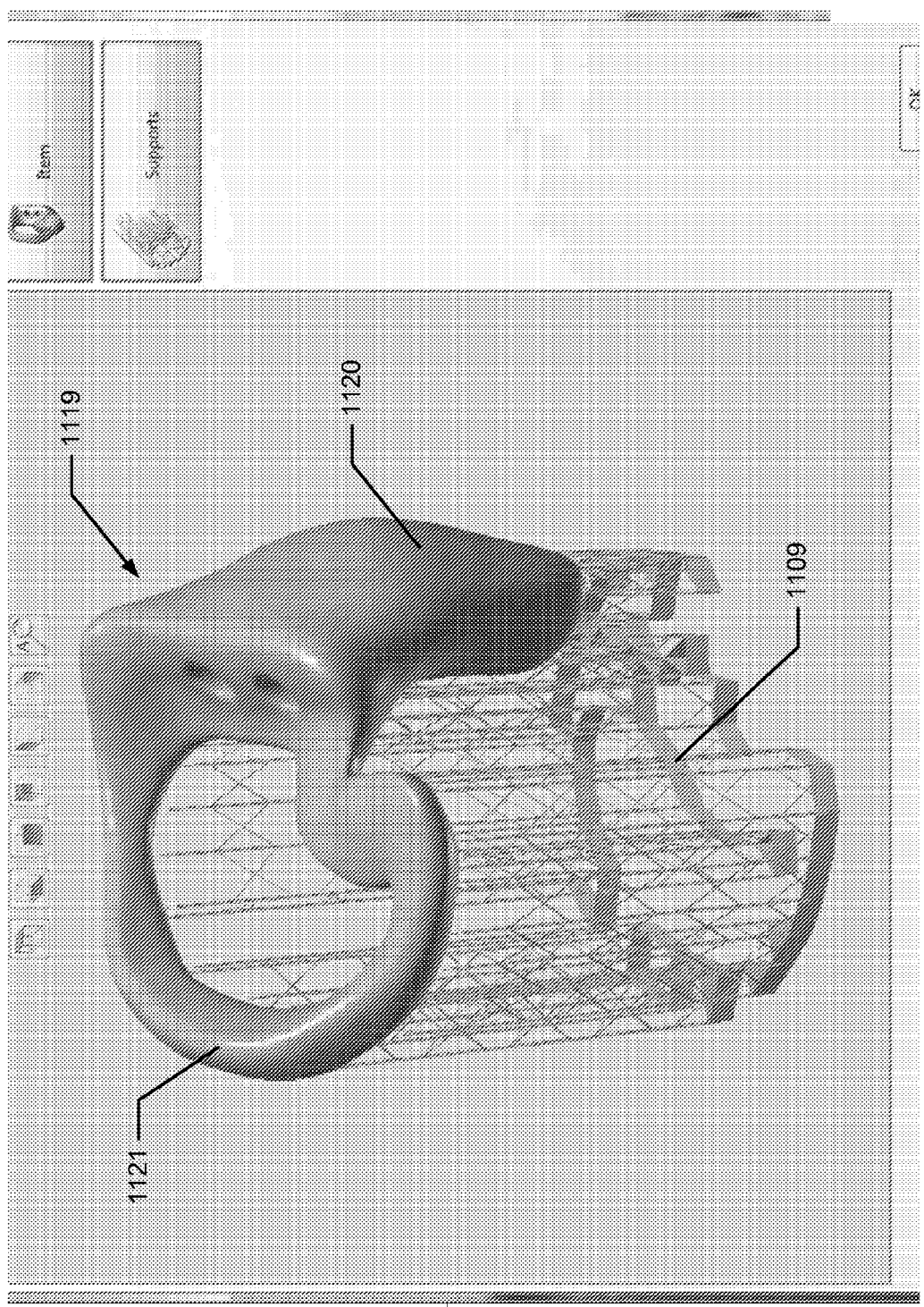
FIG. 11 shows an example of a design of a hearing device mould.

FIG. 11 shows an example of a design of a hearing device mould.

The hearing device mould can be manufactured as a design in an adaptive group. The design is in this example a hearing device mould 1119 manufactured by 3D printing, and the hearing device mould is supported by support means 1109. The hearing device mould comprises a part 1120 which is adapted to fit into the ear canal and a part 1121 which is adapted to fit in the outer part of the ear.

Figure 12A:
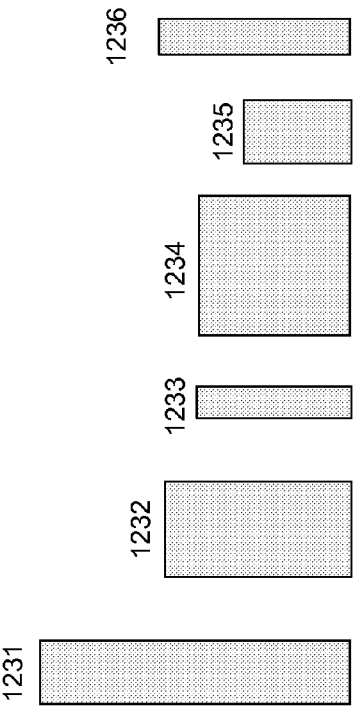
FIG. 12 shows an example of an arrangement of designs in a batch

FIG. 12 shows an example of an arrangement of 3D designs in a batch. For simplicity each 3D design and the batch are illustrated in a cross sectional view showing only height and one dimension in the batch plane. FIG. 12a shows a group 1230 of 3D designs 1231-1236 which are to be arranged on the production batch such that the batch height is as small as possible while the projection area of the designs in the batch is kept at a minimum.

Initially, the virtual designs are arranged in a virtual batch in such a way that each design has its minimum height. This allows for a determining of the minimal batch height 1237 as indicated in FIG. 12b.

Subsequently, the virtual designs 1233, 1235, and 1236 are rotated in the virtual batch relative to the batch plane such that their projection area in the batch plane is reduced while the height of each virtual design is kept under said minimal batch height. A translation of the virtual designs in the batch plane is also performed and the resulting arrangement of the virtual designs as seen in FIG. 12c. The rotation and translation provides as more compact arrangement of the designs which may reduce the material consumption when the designs are manufactured in a production batch.

Figure 12B:
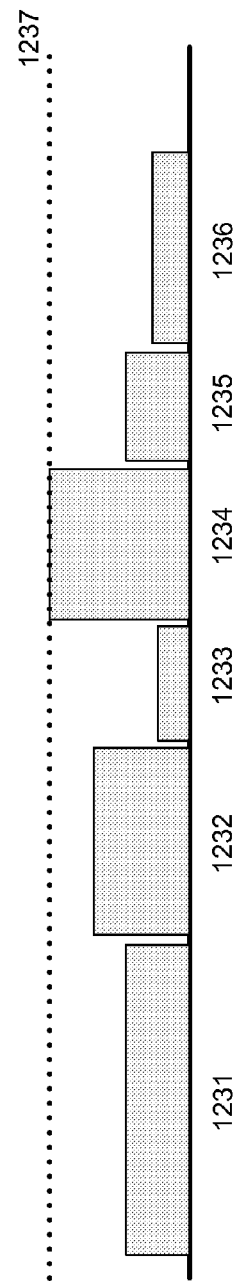
Figure 12C:
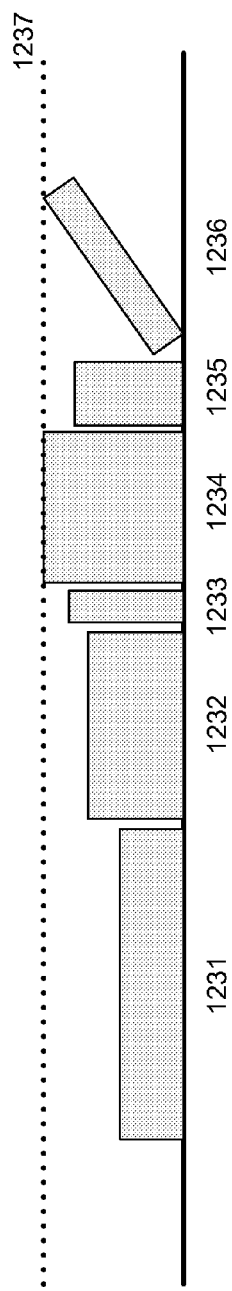
Figure 13A:
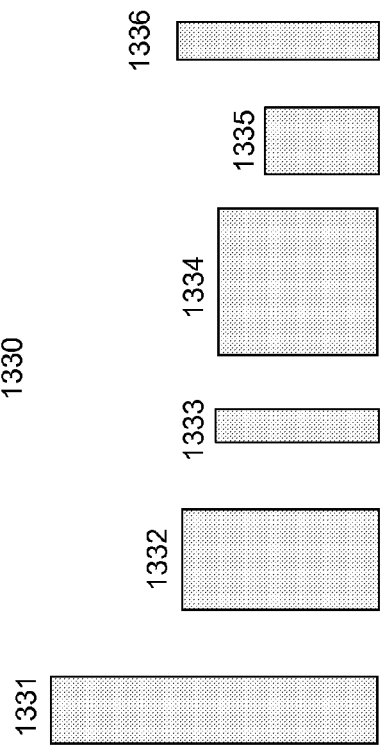
FIG. 13 shows an example of an arrangement of designs in a batch, where the arrangement is made according to a rule In the following description, reference is made to the accompanying figures, which show by way of illustration how the invention may be practiced.

FIG. 13 shows an example of an arrangement of a group of designs, where the arrangement is made according to a rule. For simplicity each 3D design and the batch are illustrated in a cross sectional view showing only height and one dimension in the batch plane. The group 1330 of designs is identical to the group 1230 of designs depicted in FIG. 12a-12c.

The designs are initially arranged to determine the minimal batch height 1337 as described in relation to FIG. 12b.

Figure 13B:
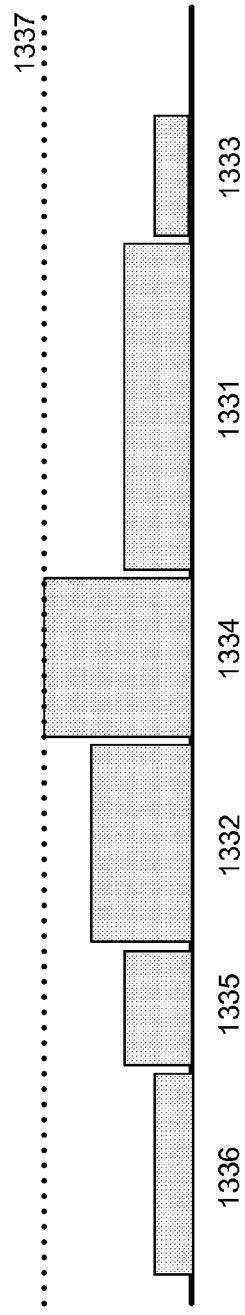
Figure 13C:
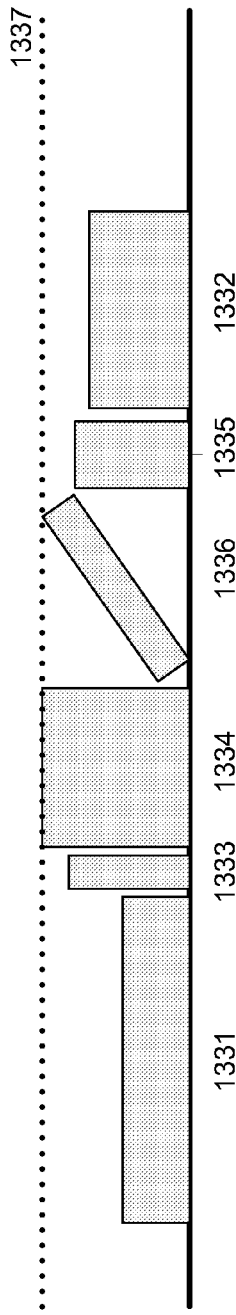

In FIG. 13b a rule dictating that the highest designs must be arranged in the center of the group has been applied to the arrangement of the designs illustrated in FIG. 12b. That is, before the rotation and translation of the designs which lead to the arrangement of FIG. 12c. When applying this rule to the arrangement of FIG. 12b, the order of designs (reading from the left side of the figure) is changed from 1231, 1232, 1233, 1234, 1235, 1236 to 1336, 1335, 1332, 1334, 1331, 1333, thereby providing that the highest design 1234, 1334 is located in the center of the group while the lower designs 1336, 1333 are located at the edge of the group In FIG. 13c the same rule (dictating that the highest designs must be arranged in the center of the group) has been applied to the arrangement of the designs illustrated in FIG. 12c. That is, after the rotation of the virtual designs relative to the batch plane. After the rotation, the designs 1333 and 1336 are no longer the lowest and when applying this rule to the arrangement of FIG. 12c, the order of designs (reading from the left side of the figure) is changed from 1231, 1232, 1233, 1234, 1235, 1236 to 1331, 1333, 1334, 1336, 1335, 1332.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

It should be emphasized that the term "according to any of the preceding claims" may be interpreted as meaning "according to any one or more of the preceding claims", such that the limitations of one or several dependent claims may be read into an independent claim.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A computer-implemented method of arranging three-dimensional virtual designs configured to be manufactured as physical designs on a production batch, the method comprising:
   providing the virtual designs, where each virtual design is based on a three-dimensional representation of an object, and where at least a number of the virtual designs belongs to a group, where the virtual designs in a respective group satisfy at least one common criterion;
   arranging said virtual designs relative to the production batch;
   allocating a first virtual design belonging to a first group at a first arbitrary position on the production batch;
   allocating a second virtual design belonging to a second group at a second arbitrary position different from the first arbitrary position on the production batch;
   allocating a third virtual design belonging to the first group at a third arbitrary position, which is different from the first and the second arbitrary positions on the production batch, and which is in the vicinity of the first arbitrary position;
   allocating each successive virtual design belonging to a group at an arbitrary position, which is different from all the previous positions, and which is in the vicinity of its group members on the production batch;
   continuously evaluating whether there is more space left on the production batch, and whether there are further virtual designs to be manufactured;
   if there is more space left on the production batch, allocating the further virtual designs according to the above step of allocating successive virtual designs;
   if there is no more space left on the product batch, stopping the allocating of virtual designs and finalizing the arrangement.

2. The computer-implemented method according to claim 1, wherein the method comprises automatically allocating each virtual design belonging to a respective group to an area for the respective group on the production batch, where the area adapts to the group, such that each virtual design belonging to a respective group is allocated in a position on the production batch such that the physical design is arranged physically together with its respective group on the production batch.

3. The computer-implemented method according to claim 1, wherein the virtual designs are three dimensional designs.

4. The computer-implemented method according to claim 1, wherein the manufacturing process comprises one of the following:
   3D printing;
   milling;
   moulding;
   sintering.

5. The computer-implemented method according to claim 1, wherein the physical designs are of dental restorations.

6. The computer-implemented method according to claim 1, wherein the physical designs are configured to comprise more than one single part.

7. The computer-implemented method according to claim 1, wherein the physical designs are of hearing devices for ear canals.

8. The computer-implemented method according to claim 1, wherein the production batch is a blank for milling.

9. The computer-implemented method according to claim 1, wherein the production batch is a mould for moulding.

10. The computer-implemented method according to claim 1, wherein the production batch is a plate for 3D printing.

11. The computer-implemented method according to claim 1, wherein an allocation of virtual designs on the production batch is based on at least one parameter.

12. The computer-implemented method according to claim 11, wherein the at least one parameter is:
    safety distance to a fixture of the production batch;
    minimum distance to a boundary of the production batch;
    connection thickness between virtual designs on the production batch;
    reserved space thickness on production batch; or
    sprue basement.

13. The computer-implemented method according to claim 1, wherein the at least one common criterion comprises that the virtual designs belong to one of the following:
    common laboratory;
    common clinic;
    common employee;
    common material;
    common height;
    common patient;
    common manufacturing equipment;
    common colour;
    common post-processing;
    common delivery address;
    common dentist;
    common shipping date;
    common size;
    common creation date;
    common delivery date;
    common importance level;
    common type of dental preparation; and
    common receiving date.

14. The computer-implemented method according to claim 1, wherein the first virtual design is arranged on the production batch such that there is a suitable area around it for other members of the first group.

15. The computer-implemented method according to claim 14, wherein the suitable area is determined based on a defined distance between the group members and based on a defined distance to the other groups.

16. The computer-implemented method according to claim 1, wherein the method comprises that a visual border is made between the groups.

17. The computer-implemented method according to claim 16, wherein the visual border is a dotted border between the groups.

18. The computer-implemented method according to claim 1, wherein the method comprises indicating the common criterion or an identification of the group at the group.

19. The computer-implemented method according to claim 1, wherein the method comprises taking into consideration the three dimensional shape of the virtual designs in the arrangement of the virtual designs.

20. The computer-implemented method according to claim 1, wherein arranging the virtual designs comprises determining a minimal batch height for a given number of virtual designs.

21. The computer-implemented method according to claim 1, wherein the method comprises optimizing the arrangement of the virtual designs to obtain the minimal batch height for a given number of virtual designs.

22. The computer-implemented method according to claim 1, wherein the method comprises arranging the virtual designs in a virtual batch.

23. The computer-implemented method according to claim 22, wherein the virtual designs are arranged in said virtual batch in such a manner that a longitudinal axis of an elongated virtual design defines a non-zero angle to the normal of the virtual batch plane.

24. The computer-implemented method according to claim 22, wherein the method comprises:
arranging the virtual designs in the virtual batch such that each virtual design has its smallest possible height and subsequently rotating at least some of the virtual designs relative to the virtual batch plane such that their projection area in the virtual batch plane is reduced while the height of each virtual design is kept under said minimal batch height.

25. The computer-implemented method according to claim 23, wherein the physical design comprises:
an abutment with non-parallel implant direction and insertion direction and the method comprises arranging the virtual design for the abutment in the virtual batch such that the angle between the insertion direction and the virtual batch plane substantially equals the angle between the implant direction and the virtual batch plane.

26. The computer-implemented method according to claim 22, wherein arranging the virtual designs comprises:
an in-plane movement of virtual designs in the virtual batch.

27. The computer-implemented method according to claim 1, wherein arranging the virtual designs comprises rotating at least some of the virtual designs relative to the batch plane such that their projection area in the batch plane is reduced.

28. The computer-implemented method according to claim 1, wherein arranging the virtual designs comprises:
an iterative procedure, wherein at least an in-plane movement or a rotation of the virtual designs relative to the batch plane is performed at least twice.

29. The computer-implemented method according to claim 22, wherein arranging the virtual designs comprises:
applying one or more rules to the arrangement of the virtual designs in the virtual batch.

30. The computer-implemented method according to claim 29, wherein said rule relates to a projection of virtual designs into the batch plane and/or on the full three dimensional surface of the virtual designs.

31. The computer-implemented method according to claim 29, wherein a sequence of rules is applied in the arrangement of the virtual designs.

32. The computer-implemented method according to claim 29, wherein said rule relate to a starting position, a shape of a track along which the virtual designs are placed in the virtual batch, a sorting of the virtual designs, and a direction of change in each group of virtual designs.

33. The computer-implemented method according to claim 32, wherein said sorting of the virtual designs relates to said at least one criterion, to a production tolerance, or to physical properties of the physical designs.

34. A system for arranging three-dimensional virtual designs, where said virtual designs are configured to be manufactured as physical designs on a production batch the system comprising:
an arranging device capable of arranging said virtual designs relative to the production batch using the method comprising:
providing the virtual designs, where each virtual design is based on a three-dimensional representation of an object, and where at least a number of the virtual designs belongs to a group, where the virtual designs in a respective group satisfy at least one common criterion;
arranging said virtual designs relative to the production batch;
allocating a first virtual design belonging to a first group at a first arbitrary position on the production batch;
allocating a second virtual design belonging to a second group at a second arbitrary position different from the first arbitrary position on the production batch;
allocating a third virtual design belonging to the first group at a third arbitrary position, which is different from the first and the second arbitrary positions on the production batch, and which is in the vicinity of the first arbitrary position;
allocating each successive design belonging to a group at an arbitrary position, which is different from all the previous positions, and which is in the vicinity of its group members on the production batch;
continuously evaluating whether there is more space left on the production batch, and whether there are further virtual designs to be manufactured;
if there is more space left on the production batch, allocating the further virtual designs according to the above step of allocating successive virtual designs;
if there is no more space left on the product batch, stopping the allocating of virtual designs and finalizing the arrangement;
an allocating device capable of automatically allocating each virtual design belonging to a respective group to an area for the respective group on the production batch, where the area adapts to the group.

35. The system according to claim 34, wherein the system comprises:
a model generating device capable of generating a virtual design from a three-dimensional representation of an object.

* * * * *